United States Patent [19]

Knapp

[11] Patent Number: 5,015,770

[45] Date of Patent: May 14, 1991

[54] PROCESS FOR PREPARING (HYDROCARBYLTHIO) AROMATIC AMINES

[75] Inventor: Gordon G. Knapp, Baton Rouge, La.

[73] Assignee: Ethyl Corporation, Richmond, Va.

[21] Appl. No.: 552,892

[22] Filed: Jul. 16, 1990

Related U.S. Application Data

[63] Continuation of Ser. No. 452,693, Dec. 18, 1989, abandoned, which is a continuation of Ser. No. 254,857, Oct. 7, 1988, abandoned.

[51] Int. Cl.$^5$ ............................................. C07C 149/42
[52] U.S. Cl. ................................. 564/440; 564/307; 564/315; 564/335; 564/427; 564/428; 564/430; 546/290; 548/337; 548/483; 548/484; 548/541
[58] Field of Search ............... 548/484, 541, 337, 483; 564/307, 315, 335, 430, 440, 427, 428; 546/290

[56] References Cited

U.S. PATENT DOCUMENTS

| 3,943,161 | 3/1976 | Nonaka et al. | 558/382 |
| 4,594,453 | 6/1986 | Ranken et al. | 564/440 |
| 4,751,330 | 6/1988 | Davis et al. | 564/440 |

*Primary Examiner*—Mukund J. Shah
*Assistant Examiner*—Philip Datlow
*Attorney, Agent, or Firm*—Richard J. Hammond; Patricia J. Hogan

[57] ABSTRACT

(Hydrocarbylthio)aromatic amines are prepared by reacting an aromatic amine, such as an aminobenzene, with a hydrocarbyl disulfide, such as an alkyl disulfide, in the presence of iodine, iodine monochloride, or iodine monobromide as a catalyst.

18 Claims, No Drawings

PROCESS FOR PREPARING (HYDROCARBYLTHIO) AROMATIC AMINES

This application is a continuation of application Ser. No. 452,693, filed Dec. 18, 1989, now abandoned, which is a continuation of application Ser. No. 254,857, filed Oct. 7, 1988, now abandoned.

FIELD OF INVENTION

This invention relates to (hydrocarbylthio)aromatic amines and more particularly to a process for preparing them.

BACKGROUND

As disclosed in U.S. Pat. No. 4,594,453 (Ranken et al.-I), it is known that various (hydrocarbylthio)aromatic amines are useful as intermediates in the preparation of biologically-active materials, polyurethanes, etc.; and they can be prepared by reacting an aromatic amine with a hydrocarbyl disulfide in the presence of a catalytic amount of a Lewis acid. The preferred catalysts of Ranken et al.-I are metal halides, such as aluminum chloride, boron trifluoride, boron trichloride, ferric chloride, and zinc chloride.

In the case of at least some aromatic amines, it has been found that the preferred catalysts identified by Ranken et al.-I have the disadvantages of effecting the desired hydrocarbylthiations at too slow a rate to be completely satisfactory and of sometimes providing too low a yield of product. These disadvantages can frequently be overcome by the use of the hydrogen iodide, ammonium iodide, and cuprous iodide catalysts of U.S. Pat. No. 4,670,597 (Ranken et al.-II), the metal iodide and bromide catalysts of U.S. Pat. No. 4,670,598 (Davis-I), or the iodine-promoted metal and metal halide catalysts of U.S. Pat. No. 4,751,330 (Davis-II). However, there is still a need for improvement in the reaction rates and/or yields of mono(hydrocarbylthio)-aromatic amines in the hydrocarbylthiation processes, and it would also be desirable to use a catalyst which could be recycled.

SUMMARY OF THE INVENTION

An object of this invention is to provide a novel process for preparing (hydrocarbylthio)aromatic amines.

Another object is to provide such a process wherein the reaction rates and/or yields of mono(hydrocarbylthio)aromatic amine products are improved.

A further object is to provide such a process using a recyclable catalyst.

These an other objects are attained by reacting an unbridged aromatic amine with a hydrocarbyl disulfide in the presence of iodine, iodine monochloride, or iodine monobromide as the sole catalyst.

DETAILED DESCRIPTION

Aromatic amines utilizable in the practice of the invention include (1) compounds having at least one amino group attached to a carbocyclic or heterocyclic ring of an unbridged aromatic compound, such as a benzene, naphthalene, anthracene, pyrrole, pyridine, or indole compound, and (2) reactive heterocyclic amines, such as pyrrole, indole, imidazole, etc.

The compounds may bear no substituents other than the required amino group, or they may bear substituents inert to the reaction conditions, such as one or more additional amino groups or substituents such as chloro, fluoro, alkyl, alkoxy, alkylthio aryl, aryloxy, arylthio, alkaryl) or aralkyl groups on any positions other than those to be substituted by hydrocarbylthio groups.

Useful aromatic amines include, e.g., 1,3-dimethylpyrrole, 1-methylpyrrole, 7-methylindole, aminobenzenes containing one or two amino groups, such as aniline, 3-methylaniline, 4-methylaniline, 2,4- and 2,6-dimethylanilines, 4-chloroaniline 4-(phenylthio)aniline, 4-phenoxyaniline, 2-ethylaniline, N-methylaniline, 2,4- and 2,6-diaminotoluenes, 2,6-diamino-1-ethylbenzene, etc. The preferred amines are the aminobenzenes.

Bridged aromatic amines, such as 4,4'-methylenedianiline, etc., have not been successfully employed in the practice of the invention.

Hydrocarbyl disulfides which may be reacted with the aromatic amines include saturated and unsaturated aliphatic, cycloaliphatic, and aromatic disulfides, such as methyl, ethyl, propyl, n-butyl, sec-butyl, t-butyl, allyl, cyclopentyl, cyclohexyl, phenyl, benzyl, and p-tolyl disulfides, etc. This component of the reaction mixture is generally employed in at least the stoichiometric amount required to yield the desired (hydrocarbylthio)aromatic amine and is preferably employed in an excess which permits the maximum achievable reaction rate. Most commonly, the amount of hydrocarbyl disulfide used is about 1–3, preferably 2–3 mols per mol of aromatic amine.

The reaction of the aromatic amine with the hydrocarbyl disulfide is generally conducted at a temperature in the range of about 20°–300° C., preferably about 100°–200° C., and at a pressure of atmospheric up to about 350 kPa; and, as mentioned above, it is conducted in the presence of iodine, iodine monochloride, or iodine monobromide (preferably iodine) as the sole catalyst. The catalyst is employed in catalytic amounts, generally in a catalyst/aromatic amine mol ratio of about 0.01–0.5/1, preferably about 0.01–0.2/1.

In conducting the process of the invention, it is frequently preferred to (1) heat a mixture of the catalyst and aromatic amine at a suitable temperature, usually a temperature higher than the boiling point of the disulfide to be added, e.g. about 100°–250° C., until all of the catalyst has reacted and then (2) heat the reaction mixture at reflux temperature after the disulfide has been added to effect a hydrocarbylthiation process while removing evolved hydrocarbyl thiol by-product from the reaction vessel. However, it is also satisfactory to conduct the process by simply mixing the catalyst and reactants together and heating them to the reflux temperature. An inert solvent may be employed if desired but is unnecessary.

The process of the invention, like the processes of Ranken et al.-I and -II and Davis-I and -II, results in the formation of (hydrocarbylthio)aromatic amines which are useful as intermediates in the preparation of biologically-active materials, polyurethanes, etc. It is particularly advantageous in that (1) it is characterized by higher reaction rates and/or higher yields of mono(hydrocarbylthio)aromatic amines than are obtained when other Lewis acid catalysts are employed and (2) it uses a catalyst which can be recycled.

The following examples are given to illustrate the invention and are not intended as a limitation thereof.

COMPARATIVE EXAMPLE A

A suitable reaction vessel was charged with 25 g of 4-methylaniline and 5 g of aluminum chloride, flushed with nitrogen, and heated to 170° C. Then 22 mL of dimethyldisulfide was added slowly over a 21-hour period while the temperature was maintained at 130°–142° C. The product was then dumped all at once into water whereupon the 4-methylaniline solidified. The product was extracted with toluene and the organic layer analyzed by GC. Analysis showed that the reaction resulted in only 14% conversion of the 4-methylaniline to mono(methylthio)-4-methylaniline and no co-formation of di(methylthio)4-methylaniline.

EXAMPLE I

A suitable reaction vessel was charged with 20 g or 4-methylaniline and 1.1 g of iodine, flushed with nitrogen, and heated to 148° C. Then 20 mL of dimethyldisulfide was added slowly over five hours while maintaining a temperature of 140°–150° C. The mixture was heated for a total of 21 hours. Analysis showed the following conversions of 4-methylaniline to mono-(methylthio)-4-methylaniline and di(methylthio)-4-methylaniline:

| Hours | Mono (%) | Di (%) |
|---|---|---|
| 5 | 23.5 | 0.5 |
| 21 | 62.8 | 6.2 |

EXAMPLE II

A suitable reaction vessel was charged with 20.1 g of 2,4-dimethylaniline and 1.8 g of iodine, flushed with nitrogen, and heated to 144° C. Then 15 mL of dimethyldisulfide was added over six hours at 140°–150° C., and heating was continued for a total of 23 hours. Analysis showed the following conversions of 2,4-dimethylaniline to mono(methylthio)-2,4-dimethylaniline (MM-2,4-DMA):

| Hours | MM-2,4-DMA (%) |
|---|---|
| 1.5 | 14 |
| 6 | 36 |
| 23 | 63 |

EXAMPLE III

Example II was repeated except that 21.3 g of 2,6-dimethylaniline was substituted for the 2,4-dimethylaniline and the total heating time was 25.5 hours. Analysis showed the following conversions of 2,6-dimethylaniline to mono(methylthio)-2,6-dimethylaniline (MM-2,6-DMA):

| Hours | MM-2,6-DMA (%) |
|---|---|
| 0.5 | 24 |
| 6 | 670 |
| 25.5 | 90 |

EXAMPLE IV

The product of Example III was distilled to purify the product and recover the catalyst residue. The 4.8 g of purple residue was dissolved in 25 g of 2,6-dimethylaniline, after which the solution was charged to a suitable reaction vessel which was then flushed with nitrogen and heated. Dimethyldisulfide (19.5 mL) was added over a period of two hours while maintaining the temperature at 140°–150° C., and heating was continued for a total of 17 hours. Analysis showed the following conversions of 2,6-dimethylaniline to MM-2,6-DMA:

| Hours | MM-2,6-DMA (%) |
|---|---|
| 1 | 19 |
| 2 | 33 |
| 17 | 78 |

EXAMPLE V

A suitable reaction vessel was charged with 20.4 g of 2,6-dimethylaniline and flushed with nitrogen, after which 0.7 mL of iodine monochloride was added. The mixture was then heated to 140°–150° C. and 26 mL of dimethyldisulfide was added over a period of 26 hours. Analysis showed the following conversions of 2,6-dimethylaniline to MM-2,6-DMA:

| Hours | MM-2,6-DMA (%) |
|---|---|
| 1 | 19 |
| 2 | 38 |
| 6 | 66 |
| 25 | 93 |

EXAMPLE VI

A suitable reaction vessel was charged with 20 g of 2,4-diaminotoluene and 1 g of iodine and heated to 130°–150° C. under nitrogen, after which 17 mL of dimethyldisulfide was added over period of 5.5 hours. After the 5.5 hours analysis showed that the reaction resulted in the conversion of 23.5% of the 2,4-diaminotoluene to mono(methylthio)-2,4-diaminotoluene and 1.5% conversion to di(methylthio)-2,4-diaminotoluene.

COMPARATIVE EXAMPLE B

A suitable reaction vessel was charged with 20 g of 2,4-diaminotoluene and 1.3 g of cuprous iodide and heated to 130°–150° C. under nitrogen, after which 34 mL of dimethyldisulfide was added over a period of 6.7 hours. Analysis showed the following conversions of 2,4-diaminotoluene to mono(methylthio)-2,4-diaminotoluene and di(methylthio)-2,4-diaminotoluene:

| Hours | Mono (%) | Di (%) |
|---|---|---|
| 1 | 54.9 | 12.1 |
| 2.5 | 39.1 | 53.9 |
| 3 | 31.7 | 64.3 |
| 3.5 | 21.6 | 76.4 |
| 4.7 | 11.9 | 87.1 |
| 6.7 | 3.0 | 96.0 |

Example VI and Comparative Example B demonstrate that, in the hydrocarbylthiation of aromatic diamines, iodine is a better catalyst than cuprous iodide when a mono(hydrocarbylthio) product is desired, while cuprous iodide is a better catalyst than iodine when a di(hydrocarbylthio) product is desired.

It is obvious that many variations may be made in the products and processes set forth above without departing from the spirit and scope of this invention.

What is claimed is:

1. In a process for reacting an unbridged aromatic amine with a hydrocarbyl disulfide in the presence of a Lewis acid catalyst to form a (hydrocarbylthio)aromatic amine, the improvement which comprises conducting the reaction in the presence of iodine, or iodine monobromide as the Lewis acid.

2. The process of claim 1 wherein the catalyst is iodine.

3. In a process for reacting compounds having at least one amino group attached to a carbocyclic or heterocyclic ring of an unbridged aromatic compound with a hydrocarbyl disulfide in the presence of a Lewis acid catalyst to form a mono-hydrocarbylthio) aromatic amine, the improvements comprising conducting the reaction in the presence of a catalytic amount of iodine or iodine monobromide as the Lewis acid.

4. The process of claim 3 wherein the aromatic amine is an aminobenzene.

5. The process of claim 4 wherein the aminobenzene is an aniline.

6. The process of claim 5 wherein the aniline is 4-methylaniline.

7. The process of claim 5 wherein the aniline is 2,4-dimethylaniline.

8. The process of claim 5 wherein the aniline is 2,6-dimethylaniline.

9. The process of claim 4 wherein the aminobenzene is a diaminobenzene.

10. The process of claim 9 wherein the diaminobenzene is a diaminotoluene.

11. The process of claim 3 wherein the hydrocarbyl disulfide is an alkyl disulfide.

12. The process of claim 11 wherein the alkyl disulfide is methyl disulfide.

13. The process of claim 3 wherein an aniline is reacted with methyl disulfide in the presence of iodine.

14. The process of claim 13 wherein the aniline is 4-methylaniline.

15. The process of claim 13 wherein the aniline is 2,4-dimethylaniline.

16. The process of claim 13 wherein the aniline is 2,6-dimethylaniline.

17. The process of claim 3 wherein a diaminobenzene is reacted with methyl disulfide in the presence of iodine.

18. The process of claim 17 wherein the diaminobenzene is a diaminotoluene.

* * * * *